United States Patent [19]

Sano et al.

[11] Patent Number: 4,568,699
[45] Date of Patent: Feb. 4, 1986

[54] PROCESS FOR PRODUCING OXYGEN-CONTAINING HYDROCARBON COMPOUNDS

[75] Inventors: Ken-ichi Sano; Yukimitsu Mita; Shinya Matsuhira; Tetsuo Nakajo; Hitoshi Iijima, all of Oita, Japan

[73] Assignee: Agency of Industrial Science and Technology, Tokyo, Japan

[21] Appl. No.: 739,317

[22] Filed: May 30, 1985

Related U.S. Application Data

[63] Continuation-in-part of Ser. No. 598,239, Apr. 9, 1984, abandoned.

[30] Foreign Application Priority Data

Apr. 11, 1983 [JP] Japan ................................. 58-62198

[51] Int. Cl.$^4$ ............................................. C07C 27/06
[52] U.S. Cl. .................................... 518/716; 518/700
[58] Field of Search ............................... 518/716, 700

[56] References Cited

U.S. PATENT DOCUMENTS 4,199,522 4/1980 Murchison .

FOREIGN PATENT DOCUMENTS 21241 1/1981 European Pat. Off. .
30110 6/1981 European Pat. Off. .
33212 8/1981 European Pat. Off. .
57-62231 4/1982 Japan .

Primary Examiner—Howard T. Mars
Attorney, Agent, or Firm—Browdy and Neimark

[57] ABSTRACT

A catalyst comprising a combination of rhodium, iridium and lithium supported on a carrier having a specific surface area of more than 150 m$^2$/g is disclosed for producing two carbon atom oxygenated compounds from carbon monoxide. The catalyst has high catalytic activity and high selectivity to acetic acid.

7 Claims, No Drawings

PROCESS FOR PRODUCING OXYGEN-CONTAINING HYDROCARBON COMPOUNDS

CROSS-REFERENCE TO RELATED APPLICATION

This application is a continuation-in-part application of Ser. No. 598,239 filed on Apr. 9, 1984, now abandoned.

BACKGROUND OF THE INVENTION

This invention relates to a process for producing an oxygen-containing hydrocarbon compound from carbon monoxide and hydrogen, such as, for example, synthesis gas. More particularly, the present invention concerns reaction of carbon monoxide and hydrogen in the presence of a catalyst comprising a combination of rhodium-iridium-lithium supported on a carrier having a specific surface area of more than 150 m$^2$/g.

The preparation of two-carbon atom oxygenated compounds acetic acid, acetaldehyde and ethanol from carbon monoxide and hydrogen, such as, for example, synthesis gas is known.

In general, when a gaseous mixture of carbon monoxide and hydrogen, such as synthesis gas, contacts with a catalyst, a variety of products are formed. The products include saturated aliphatic hydrocarbons ranging from methane to paraffin; unsaturated aliphatic hydrocarbons including alpha-olefin; aromatic hydrocarbons having 6-10 or more carbon atoms; alcohols ranging from methanol to higher alcohol having about 20 carbon atoms; aldehydes and fatty acids. Particulars of the products depend upon nature of the catalysts employed.

In general, it had been difficult to selectively form the desired compounds while suppressing formation of the undesirable compounds by reacting carbon monoxide with hydrogen. In order to achieve the above mentioned purpose, much research on catalysts has been made. There are many patents and patent applications on catalysts for such reaction. For example, Japanese Patent Publication (kokai) No. 55-57527; U.S. Ser. No. 551,661 dated Jan. 16, 1975 and U.S. Ser. No. 437,141 dated Jan. 28, 1974; and U.S. Pat. Nos. 4,014,913 patented on Mar. 29, 1977, 4,224,236 patented on Sept. 23, 1980 and 4,288,558 patented on Sept. 8, 1981 disclose that rhodium-containing catalysts are used for selectively producing two carbon atoms oxygenated compounds from carbon monoxide and hydrogen.

The present inventors have carried out the reaction of carbon monoxide and hydrogen in the presence of a rhodium catalyst. It was found that though the rhodium catalyst allows selective formation of two carbon atom oxygenated compounds and suppresses undesirable by-products, such as carbon dioxide, methane, etc., catalytic activity of the rhodium catalyst is low. In addition, it was also found that when the rhodium catalyst is used for the reaction between carbon monoxide and hydrogen, acetaldehyde is formed as a main component. Therefore, production of acetic acid by reacting carbon monoxide with hydrogen in the presence of the rhodium catalyst is improper. Since rhodium is expensive, it is important to improve the catalytic activity of rhodium catalyst and its selectivity to the desired products in the reaction.

SUMMARY OF THE INVENTION

The present inventors have carried out research on catalysts comprising a combination of rhodium and other elements. As a result, we found that a catalyst comprising a combination of rhodium, iridium and lithium supported on a carrier is suitable for reaction between carbon monoxide and hydrogen.

An object of this invention is to provide a catalyst of high catalytic activity and high selectivity to two carbon atom oxygenated compounds in reaction between carbon monoxide and hydrogen.

This invention relates to a process for producing acetic acid and at least one acetaldehyde and ethanol which comprises reacting carbon monoxide with hydrogen in the presence of a catalyst, said catalyst comprising a combination of rhodium, iridium and lithium supported on a catalyst having a specific surface area of more than 150 m$^2$/g, and amount of lithium employed being less than 0.5% by weight and preferably less than 0.1% by weight on the basis of the total weight of the catalyst and the carrier.

DETAILED EXPLANATION OF THE INVENTION

The catalysts employed in the practice of this invention comprise rhodium component selected from metallic rhodium, a rhodium compound or mixtures thereof; an iridium component selected from metallic iridium, iridium compounds or mixtures thereof; and lithium compounds. A compound containing rhodium, iridium and lithium, or mixture of a compound containing two of rhodium, iridium and lithium and a compound containing the other one of the three may be used as the catalyst.

Metallic rhodium and salts of rhodium having low valency are preferable as the rhodium component. Examples of the rhodium compounds include inorganic acid salts, such as rhodium chloride, rhodium bromide, rhodium iodide, sodium rhodiate chloride, ammonium rhodiate chloride, rhodium nitrate, and rhodium sulfate; rhodium oxides; organic acid salts, such as rhodium acetate, rhodium formate and rhodium oxalate; ammine complex salts of rhodium; and cluster of rhodium.

Metallic iridium and salts of iridium having low valency are preferable as the iridium component. Examples of the iridium compounds include inorganic acid salts, such as iridium chloride, iridium bromide, iridium iodide, sodium iridate chloride, ammonium iridate chloride, and iridium nitrate; oxides of iridium; organic acid salts, such as iridium formate and iridium oxalate; ammine complex salts of iridium and cluster of iridium.

Oxide, inorganic acid salts and complex salts of lithium may be used as the lithium component. The lithium ion may be bonded to the compounds containing rhodium and/or iridium. Examples of the lithium compounds include inorganic acid salts, such as halides, sulfate, nitrate, carbonate of lithium; lithium oxide; lithium hydroxide; and organic acid salts, such as acetate, formate and oxalate of lithium.

The catalysts of this invention is supported on a carrier having a specific surface area of more than 150 m$^2$/g, and preferably 250 m$^2$/g–1000 m$^2$/g. Water soluble compounds or solvent soluble compounds are preferable as the rhodium component, iridium component and lithium component in order to make supporting of the catalyst on a carrier easier.

PREFERABLE PREPARATION OF CATALYSTS

The rhodium, iridium and lithium compounds are dissolved in water or an organic solvent, such as n-hexane, an alcohol, acetone. Porous inorganic carrier having a specific surface area of more than 150 m$^2$/g is added to the solution. The catalyst is supported on the catalyst by impregnation method, ion exchange method or other known methods. Thereafter, the catalyst-supported carrier is subject to reduction or thermal treatment. The three components constituting the catalyst may be supported on a carrier at the same time. The three components may be successively supported on a carrier while subjecting the components to reduction or thermal treatment.

It is preferable that the rhodium component in the catalyst obtained thus is reduced to metallic rhodium in order to promote activity of the catalyst. The reduction may be carried out under a hydrogen gas, mixed gas of hydrogen and carbon monoxide, or under a hydrogen gas or the mixed gas diluted with an inert gas, such as nitrogen, helium or argon.

The reduction temperature may be in the range of 100°–600° C., and preferably 250°–550° C. The reduction may be carried out by gradually raising the temperature in order to keep the activity of each component optimal.

The rhodium compounds may be reduced with a reducing agent, such as methanol, hydrazine, formalin, etc.

The proportions of each catalytic component in the catalyst is not critical. When the catalyst is supported on a carrier, the amount of rhodium employed may be in the range of 0.01–15% by weight, and preferably 0.1–10% by weight on the basis of the total weight of the catalyst and the carrier in terms of metal by considering specific surface area of more than 150 m$^2$/g of the carrier.

The atomic ratio of iridium to rhodium (Ir/Rh) may be in the range of 0.001–10, and preferably 0.01–3.

The atomic ratio of lithium to rhodium (Li/Rh) may be in the range of 0.001–10, and preferably 0.01–1.

Examples of the carriers include silica, activated alumina, titanium oxides, thorium oxides, activated carbon, zeolites and mixtures thereof. Silica is preferable. Carriers in any form, such as in powder, pellets, or particles may be used.

The reaction may be carried out in a gaseous phase. For example, a starting material gas comprising carbon monoxide and hydrogen may be passed through a stationary bed type reactor containing the catalyst. The starting material gas may contain carbon dioxide, nitrogen argon, helium, steam, methane and the like with carbon monoxide and hydrogen.

The reactors may be of fluidized bed type or mobile bed type.

The reaction may be carried out in a liquid phase. In this case, the starting material gas may be passed through a suspension in which the catalyst is dispersed in a suitable solvent.

The reaction conditions may vary depending on the reactor types. In general, the reaction conditions in the case of using a stationary bed type reactor are as follows:

The mol ratio of carbon monoxide to hydrogen may be in the range of 20:1 to 1:5, and preferably 10:1 to 1:3.

The reaction temperature may be in the range of 150–450°° C., and preferably 200°–350° C.

The reaction pressure may be in the range of 1–300 atm, and preferably 20–200 atm.

The space velocity, SV may be in the range of 100–10$^6$H$^{-1}$, and preferably 1,000–10$^5$H$^{-1}$.

The present invention is further illustrated by the following non-limiting Examples and Comparative Runs.

All percentages and parts in these Examples and Comparative Runs are by weight, unless otherwise specified.

EXAMPLE 1

Rhodium chloride (RhCl$_3$. 3H$_2$O)(2.553 g), iridium chloride (IrCl$_4$. H$_2$O)(0.428 g) and lithium chloride (0.025 g) were dissolved in 23 ml of pure water. To the solution was added 18.7 g of silica gel having a specific surface area of 290 m$^2$/g (Fuji Davison Chemical Kabushiki Kaisha *57) which had been baked at 400° C. for 2 hours. The solution was uniformly impregnated into the silica gel. The mixture was dried at room temperature for 1 hour and at 80° C. for additional 20 hours while stirring the mixture sometimes. The resulting catalyst was placed into silica glass reactor for reduction. The catalyst was hydrogen-reduced at 450° C. for 2 hours while passing a hydrogen gas through the reactor at a rate of 15 Nl/hr. The results are shown in Table 1.

EXAMPLES 2–4

The procedures of Example 1 were repeated using catalysts in amount given in Table 1 and the reaction conditions given in Table 1. The results are shown in Table 1.

EXAMPLES 5–6

The procedures of Example 1 were repeated except that catalytic components in amounts given in Table 1 were used.

EXAMPLE 7

The procedure of Example 1 was repeated except that lithium nitrate was used in place of lithium chloride.

EXAMPLES 8–10

The procedures of Examples were repeated so that the catalysts containing components in amounts given in Table 1 were prepared.

Comparative Run 1

The procedure of Example 1 was repeated except that lithium chloride was not used.

Comparative Run 2

The procedure of Example 1 was repeated except that iridium chloride was not used and lithium chloride (0.138 g) was used.

Comparative Run 3

The procedure of Example 1 was repeated except that 1.87 g of lithium chloride was used. The results are shown in Table 1.

Comparative Run 4

The procedure of Example 7 was repeated except that silica gel having specific surface area of 40 m$^2$/g. The results are shown in Table 1.

Comparative Run 5

The procedure of Example 1 was repeated except that 1.510 g of zirconium chloride (ZrCl$_4$) was used instead of lithium chloride. The results are shown in Table 1.

Comparative Run 6

5 Grams of the catalyst supported on the carrier of Example 7 was added in 100 ml of water. The mixture of water and the catalyst was used as a catalyst.

Comparative Run 7

The procedure of Example 1 was repeated except that lithium chloride was not used. The results are shown in Table 1.

Comparative Run 8

The procedure of Example 1 was repeated except that the following catalytic components were used:

| | |
|---|---|
| RhCl$_3$.3H$_2$O | 2.553 g |
| MgCl$_2$ | 0.188 g |
| NaCl | 0.203 g |

The results are shown in Table 1.

Each of the catalysts of Examples 1-10 and Comparative Runs 1-5 and 7-8 was charged into U-shaped stainless steel reactor. Starting material gas (CO/H$_2$:2/1) was passed through each reactor at 290° C. and 100 Kg/cm$^2$. G at a rate of 75 Nl/hr. The reaction products were cooled under pressure and corrected. Gas chromatograph analysis showed that the products contained components given in Table 1.

The catalyst (solution) of Comparative Run 6 was placed in autoclave. The reaction was effected 265° C. for 2 hours while sparging a starting material gas (CO/H$^2$:2/1) through the solution at 50 Kg/cm$^2$G.

$$\text{Selectivity (\%)} = \frac{\text{mol of carbon monoxide converted to each product}}{\text{mol of carbon monoxide consumed}}$$

In Table 1, selectivity of C$_2$—O means the total selectivity each of acetic acid, acetaldehyde and ethanol.

TABLE 1

| Example or Comparative Run | Reaction temperature (°C.) | Reaction pressure (Kg/cm$^2$G) | mol ratio of starting material gas (CO/H$_2$) | SV of CO + H$_2$ (Nl/hr.) | amount of catalyst employed (ml) | Number of hours after reaction |
|---|---|---|---|---|---|---|
| Example 1 | 290 | 100 | 2/1 | 75 | 10 | 4 |
| Example 2 | 300 | 100 | 9/1 | 75 | 15 | 10 |
| Example 3 | 280 | 100 | 9/1 | 75 | 20 | 11.5 |
| Example 4 | 290 | 100 | 2/1 | 75 | 10 | 4 |
| Example 5 | 290 | 100 | 2/1 | 75 | 10 | 4 |
| Example 6 | 290 | 100 | 2/1 | 75 | 10 | 4 |
| Example 7 | 290 | 100 | 2/1 | 75 | 10 | 4 |
| Example 8 | 300 | 100 | 9/1 | 100 | 10 | 4 |
| Example 9 | 280 | 100 | 9/1 | 100 | 10 | 4 |
| Example 10 | 280 | 100 | 9/1 | 100 | 10 | 4 |
| Comp. Run 1 | 300 | 100 | 2/1 | 150 | 30 | 4 |
| Comp. Run 2 | 300 | 100 | 2/1 | 150 | 30 | 4 |
| Comp. Run 3 | 290 | 100 | 2/1 | 75 | 10 | 4 |
| Comp. Run 4 | 290 | 100 | 2/1 | 75 | 10 | 4 |
| Comp. Run 5 | 290 | 100 | 2/1 | 75 | 10 | 4 |
| Comp. Run 6 | 265 | 50 | 2/1 | — | 10 | 2 |
| Comp. Run 7 | 290 | 100 | 2/1 | 75 | 10 | 4 |
| Comp. Run 8 | 280 | 100 | 2/1 | 75 | 10 | 4 |

| Example or Comparative Run | Catalyst composition (wt %) | | | | | | Selectivity (%) | | | | | |
|---|---|---|---|---|---|---|---|---|---|---|---|---|
| | Rh | Ir | Li | Zr | Mg | Na | C$_2$—O | acetic acid | acetaldehyde | ethanol | methanol | hydrocarbons of C$_2$ or more |
| Example 1 | 5.0 | 1.17 | 0.02 | | | | 86.5 | 51.5 | 28.4 | 6.5 | 8.5 | 2.0 |
| Example 2 | 5.0 | 1.17 | 0.02 | | | | 89.8 | 64.2 | 19.5 | 6.2 | 3.3 | 3.6 |
| Example 3 | 5.0 | 1.17 | 0.02 | | | | 91.4 | 71.4 | 16.6 | 3.4 | 2.7 | 2.6 |
| Example 4 | 5.0 | 1.17 | 0.01 | | | | 85.1 | 45.3 | 32.3 | 7.6 | 10.3 | 1.9 |
| Example 5 | 5.0 | 0.59 | 0.02 | | | | 84.9 | 46.8 | 31.2 | 6.9 | 9.9 | 2.0 |
| Example 6 | 5.0 | 0.59 | 0.04 | | | | 83.8 | 52.4 | 24.6 | 6.8 | 3.3 | 3.2 |
| Example 7 | 5.0 | 1.17 | 0.04 | | | | 84.7 | 53.5 | 24.6 | 6.5 | 8.1 | 2.6 |
| Example 8 | 5.0 | 0.055 | 0.0045 | | | | 89.1 | 76.7 | 11.6 | 0.8 | 1.7 | 3.6 |
| Example 9 | 5.0 | 0.055 | 0.0025 | | | | 88.7 | 65.2 | 21.5 | 0.2 | 2.8 | 5.2 |
| Example 10 | 6.0 | 0.11 | 0.009 | | | | 88.3 | 67.2 | 18.7 | 0.2 | 2.4 | 5.8 |
| Comp. Run 1 | 5.0 | 1.17 | — | | | | 77.3 | 32.3 | 37.0 | 8.0 | 16.4 | 2.7 |
| Comp. Run 2 | 5.0 | — | 0.11 | | | | 74.3 | 41.9 | 23.3 | 9.1 | 12.7 | 4.8 |
| Comp. Run 3 | 5.0 | 1.17 | 1.50 | | | | 51.0 | 30.6 | 15.5 | 4.9 | 3.1 | 14.9 |
| Comp. Run 4 | 5.0 | 1.17 | 0.04 | | | | 46.4 | 24.5 | 12.6 | 9.3 | 7.5 | 9.2 |
| Comp. Run 5 | 5.0 | 1.17 | | 2.96 | | | 62.5 | 33.0 | 25.0 | 4.5 | 2.0 | 10.3 |
| Comp. Run 6 | 5.0 | 1.17 | 0.04 | | | | 17.8 | 6.0 | 10.2 | 1.7 | 0.1 | 51.0 |
| Comp. Run 7 | 5.0 | 1.17 | | | | | 54.1 | 15.6 | 19.5 | 19.0 | 8.3 | 7.9 |
| Comp. Run 8 | 5.0 | | | | 0.24 | 0.4 | 45.3 | 21.2 | 20.9 | 3.2 | 2.3 | 40.5 |

What is claimed is:

1. A process for producing acetic acid and at least one acetaldehyde and ethanol which comprises reacting, in the gaseous phase, carbon monoxide with hydrogen in the presence of a catalyst, said catalyst comprising a combination of rhodium, iridium and lithium supported on a carrier having a specific surface area of more than 150 m$^2$/g, and amount of lithium employed being less than 0.5% by weight on the basis of the total weight of the catalyst and the carrier.

2. The process as defined in claim 1 wherein said catalyst comprises a rhodium component selected from metallic rhodium, a rhodium compound or mixtures thereof; an iridium component selected from metallic iridium, iridium compounds or mixtures thereof; and lithium compounds.

3. The process as defined in claim 1 wherein said catalyst comprises a compound containing rhodium, iridium and lithium.

4. The process as defined in claim 1 wherein said catalyst comprises a mixture of a compound containing two of rhodium, iridium and lithium and a compound containing the other one of the three.

5. The process as defined in claim 1 wherein said carrier is selected from silica, activated alumina, titanium oxides, thorium oxides, activated carbon, zeolites or mixtures thereof.

6. The process as defined in claim 1 wherein said carrier is silica.

7. The process as defined in claim 4 wherein the amount of rhodium employed is in the range of 0.01–15% by weight on the basis of weight of the catalyst-supported carrier in terms of metal.

* * * * *